US009760683B2

(12) United States Patent
Taniguchi et al.

(10) Patent No.: US 9,760,683 B2
(45) Date of Patent: Sep. 12, 2017

(54) MONITORING APPARATUS

(71) Applicant: NIHON KOHDEN CORPORATION, Shinjuku-ku, Tokyo (JP)

(72) Inventors: Hiroyuki Taniguchi, Tokyo (JP); Kazuya Nagase, Tokyo (JP); Rie Tanaka, Tokyo (JP)

(73) Assignee: NIHON KOHDEN CORPORATION, Shinjuku-Ku, Tokyo (JP)

( * ) Notice: Subject to any disclaimer, the term of this patent is extended or adjusted under 35 U.S.C. 154(b) by 0 days.

(21) Appl. No.: 14/380,663

(22) PCT Filed: Feb. 14, 2013

(86) PCT No.: PCT/JP2013/054247
§ 371 (c)(1),
(2) Date: Aug. 22, 2014

(87) PCT Pub. No.: WO2013/125606
PCT Pub. Date: Aug. 29, 2013

(65) Prior Publication Data
US 2015/0199486 A1 Jul. 16, 2015

(30) Foreign Application Priority Data

Feb. 23, 2012 (JP) ................................ 2012-037190

(51) Int. Cl.
*G06F 19/00* (2011.01)
*A61B 5/0205* (2006.01)
(Continued)

(52) U.S. Cl.
CPC .......... *G06F 19/3406* (2013.01); *A61B 5/021* (2013.01); *A61B 5/0205* (2013.01);
(Continued)

(58) Field of Classification Search
None
See application file for complete search history.

(56) References Cited

U.S. PATENT DOCUMENTS 6,188,407 B1   2/2001   Smith et al.
7,371,214 B2   5/2008   Kouchi et al.
(Continued)

FOREIGN PATENT DOCUMENTS

CN   1678238 A   10/2005
JP   2716020 B2   2/1998
(Continued)

OTHER PUBLICATIONS

International Search Report and Written Opinion of the International Search Report for PCT/JP2013/054247 dated Apr. 26, 2013.
(Continued)

*Primary Examiner* — Michelle Chin
(74) *Attorney, Agent, or Firm* — Pearne & Gordon LLP

(57) ABSTRACT

It is formed, on a display, a first display region in which at least one of measurement signals related to biological information of a subject is displayed in real time. It is formed, on the display, a second display region at a position where is not overlapping with the first display region. A first history display region and a second history display region are displayed in the second display region. The first history display region displays a history related to a first one of the measurement signals, and the second history display region displaying a history related to a second one of the measurement signals.

11 Claims, 5 Drawing Sheets

(51) Int. Cl.
*A61B 5/044* (2006.01)
*A61B 5/00* (2006.01)
*A61B 5/021* (2006.01)
*A61B 5/0464* (2006.01)

(52) U.S. Cl.
CPC ............ *A61B 5/044* (2013.01); *A61B 5/7282* (2013.01); *A61B 5/743* (2013.01); *A61B 5/746* (2013.01); *A61B 5/0464* (2013.01); *A61B 5/742* (2013.01)

(56) References Cited

U.S. PATENT DOCUMENTS

| | | |
|---|---|---|
| 2003/0135087 A1 | 7/2003 | Hickle et al. |
| 2006/0074321 A1 | 4/2006 | Kouchi et al. |
| 2009/0216138 A1 | 8/2009 | Arand et al. |
| 2011/0004071 A1 | 1/2011 | Faiola et al. |
| 2011/0092838 A1 | 4/2011 | Helfenbein et al. |
| 2011/0307891 A1* | 12/2011 | Orr .................... G06F 1/26 718/100 |
| 2012/0075103 A1 | 3/2012 | Powell et al. |

FOREIGN PATENT DOCUMENTS

| | | |
|---|---|---|
| JP | 2001-128945 A | 5/2001 |
| JP | 2006-180979 A | 7/2006 |
| JP | 2008-535540 A | 9/2008 |
| JP | 2009-160233 A | 7/2009 |
| JP | 2009-189443 A | 8/2009 |
| WO | 2006/094109 A1 | 9/2006 |
| WO | 2010/144413 A1 | 12/2010 |

OTHER PUBLICATIONS

Japanese Office Action for the related Japanese Patent Application No. 2012-037190 dated Jul. 7, 2015.
European Office Action for Application No. 13710905.4 dated Jun. 9, 2016.
Chinese Office Action for Application No. 201380010855.6 dated Apr. 27, 2016.

* cited by examiner

MONITORING APPARATUS

This application is a U.S. national phase filing under 35 U.S.C. §371 of PCT Application No. PCT/JP2013/054247, filed Feb. 14, 2013, and which in turn claims priority under 35 U.S.C. §119 to Japanese Patent Application No. JP2012-037190, filed Feb. 23, 2012, the entireties of which are incorporated by reference herein.

TECHNICAL FIELD

The present invention relates to a monitoring apparatus which is to be installed in a medical institution or the like to display measurement data related to biological information of a subject.

BACKGROUND ART

As an apparatus of this kind, known is an apparatus in which measurement data of biological information obtained from a subject can be displayed in real time on a screen of a displaying section, and also history information of the measurement data can be displayed (for example, see Patent Documents 1 and 2).

For example, the history information includes the waveform of a biological signal and measurement value of the subject at a certain time point, and alarm information which is issued in a case where measurement data indicates a situation in which attention to a certain subject is required.

CITATION LIST

Patent Document

[Patent Document 1] Japanese Patent No. 2,716,020B2
[Patent Document 2] Japanese Patent Publication No. 2006-180979A

SUMMARY OF THE INVENTION

Technical Problem

In the apparatuses disclosed in Patent Documents 1 and 2, when an operator performs a prescribed operation, a dedicated screen for displaying history information of measurement data appears on the whole of the displaying section. The operator seeks a desired measurement result or alarm information from the displayed history information.

The dedicated screen for displaying history information occupies the whole displaying section. During a period when the operator seeks or browses desired information, therefore, measurement data of biological information of the subject cannot be viewed in real time. The history information is updated from moment to moment depending on the measurement result. Therefore, also the display contents of the history information screen are updated. This may obstruct the seeking or browsing work of the operator.

Therefore, it is an object of the invention to provide a technique for, while ensuring real-time visibility of measurement signals related to biological information, improving the efficiency of seeking or browsing history information of measurement data.

Solution to Problem

In order to achieve the above object, as one aspect of the invention, there is provided a monitoring apparatus, comprising:

a display;

a receiver, configured to receive a plurality of kinds of measurement signals which are related to biological information of a subject;

a first display region former, configured to form, on the display, a first display region in which at least one of the measurement signals is displayed in real time;

a second display region former, configured to form, on the display, a second display region at a position where is not overlapping with the first display region; and a history presenter, configured to form, in the second display region, a first history display region displaying a history related to a first one of the measurement signals, and a second history display region displaying a history related to a second one of the measurement signals.

According to the above configuration, in order to browse a past measurement history of specific biological information of the subject, the second display region is formed at a position where is not overlapping with the first display region where measurement signals are displayed in real time. Therefore, real-time viewing of measurement signals is not impeded even during a work of seeking or browsing a history. Moreover, since history displays respectively related to plural kinds of measurement signals can be displayed side by side in the second display region, the work of seeking or browsing a history can be efficiently performed while monitoring in real time the measurement signals.

In a case where data corresponding to a certain time in the history related to the first one of the measurement signals is specified in the first history display region, the history presenter may be configured to display, in the second history display region, data corresponding to the certain time in the history related to the second one of the measurement signals.

Generally, measurement data of biological information at a timing when an alarm is issued tend to exhibit a strong mutual correlation. According to the above configuration, simply by specifying data required to be checked in connection with the first one of the measurement signals in the first history display region, data at a corresponding time in the second one of the measurement signals is displayed in the second history display region. Therefore, it is possible to provide a display mode which is excellent in listing property, and in which a history can be efficiently sought or browsed.

The history presenter may be configured to stop updating of the history displayed in the first history display region and the history displayed in the second history display region, while the data corresponding to the certain time is displayed. In this case, the browsing work is not obstructed even when an event requiring the updating of the displayed history is occurred by measurement signals sequentially received.

The monitoring apparatus as set forth in any one of the preceding claims, wherein the history presenter is configured to cause a measurement signal related to biological information having a strong correlation with biological information related to the first one of the measurement signals, to be the second one of the measurement signals.

The history related to the first one of the measurement signals and the history related to the second one of the measurement signals may be respectively displayed as a form of any one of forms of waveform, character, graph and chart (for example, workflow or illustration of the diagnostic method). Particularly in a case where display modes of the respective history display regions are different from each other, there is a remarkable merit because the different display modes can be arranged side by side in the second display region, and can be prepared at one view.

A position of the first history display region and a position of the second history display region may be respectively changeable within the second display region. In this case, the layout of the history display regions on the display can be changed as required.

The second display region former may be configured to cause the second display region to appear on the display in accordance with a prescribed operation. Here, a displayed size of the first display region former may be reduced so as to avoid the second display region appeared. In this case, when it is not required to browse a history, the first display region in which measurement signals are displayed in real time can be displayed on whole of the display. Therefore, the real-time visibility of measurement signals is improved.

DESCRIPTION OF EMBODIMENTS

Embodiments of the invention will be described below in detail with reference to the accompanying drawings.

Figure 1:
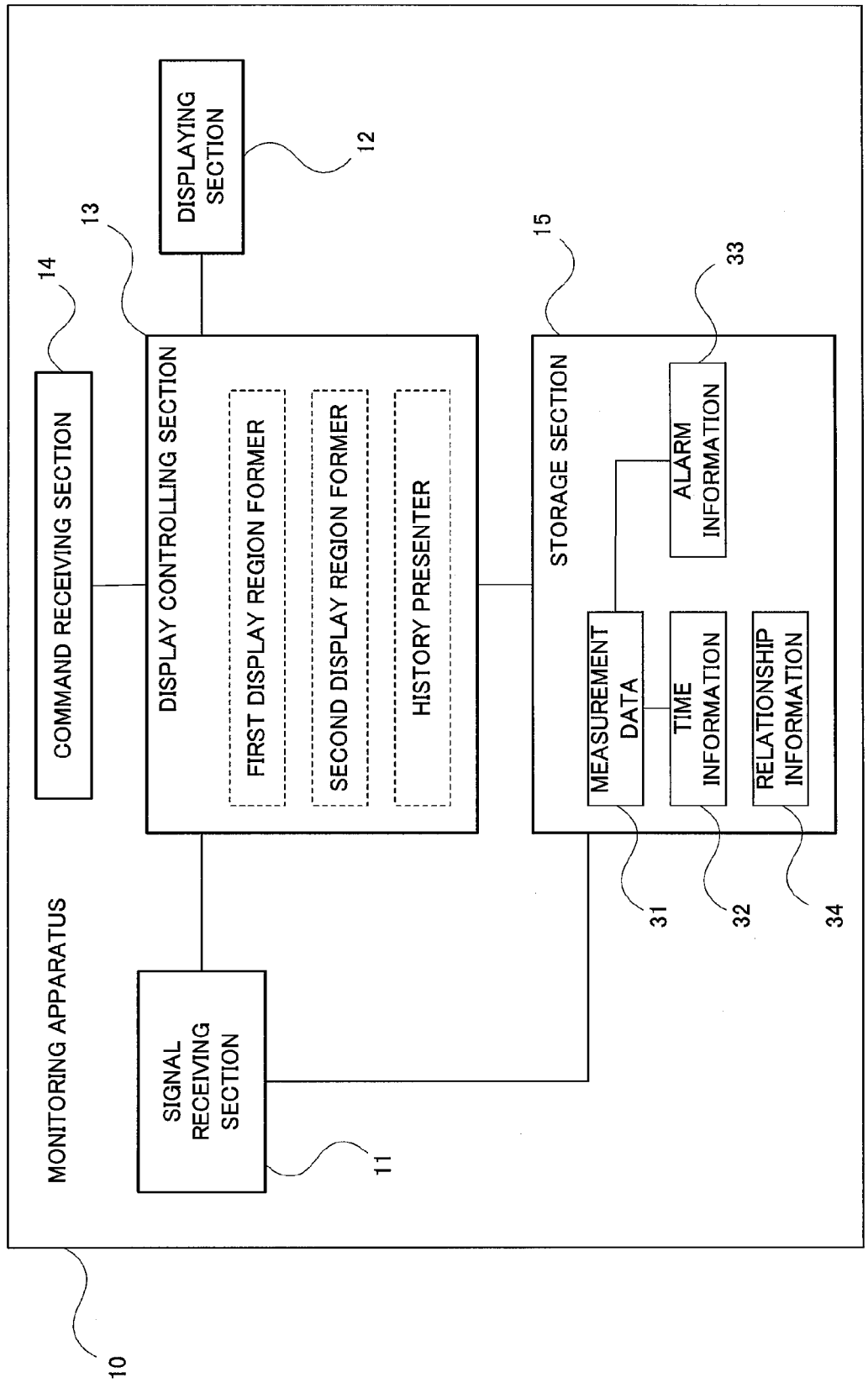
FIG. 1 is a functional diagram showing a configuration of a monitoring apparatus according to one embodiment of the invention.

FIG. 1 is a functional block diagram showing a configuration of a monitoring apparatus 10 according to one embodiment of the invention. The monitoring apparatus 10 includes a signal receiving section 11, a displaying section 12, a display controlling section 13, an command receiving section 14, and a storage section 15.

The signal receiving section 11 as one example of a receiver receives a plurality of kinds of measurement signals which are related to biological information, and which are acquired through a biological information acquiring means (electrodes, a cuff, various sensors, or the like) attached to a subject, directly or by way of a network. Examples of biological information of the subject are pulse rate, electrocardiogram, blood pressure, oxygen saturation, respiratory volume, concentration of carbon dioxide in the expired gas, and so on.

Figure 2:
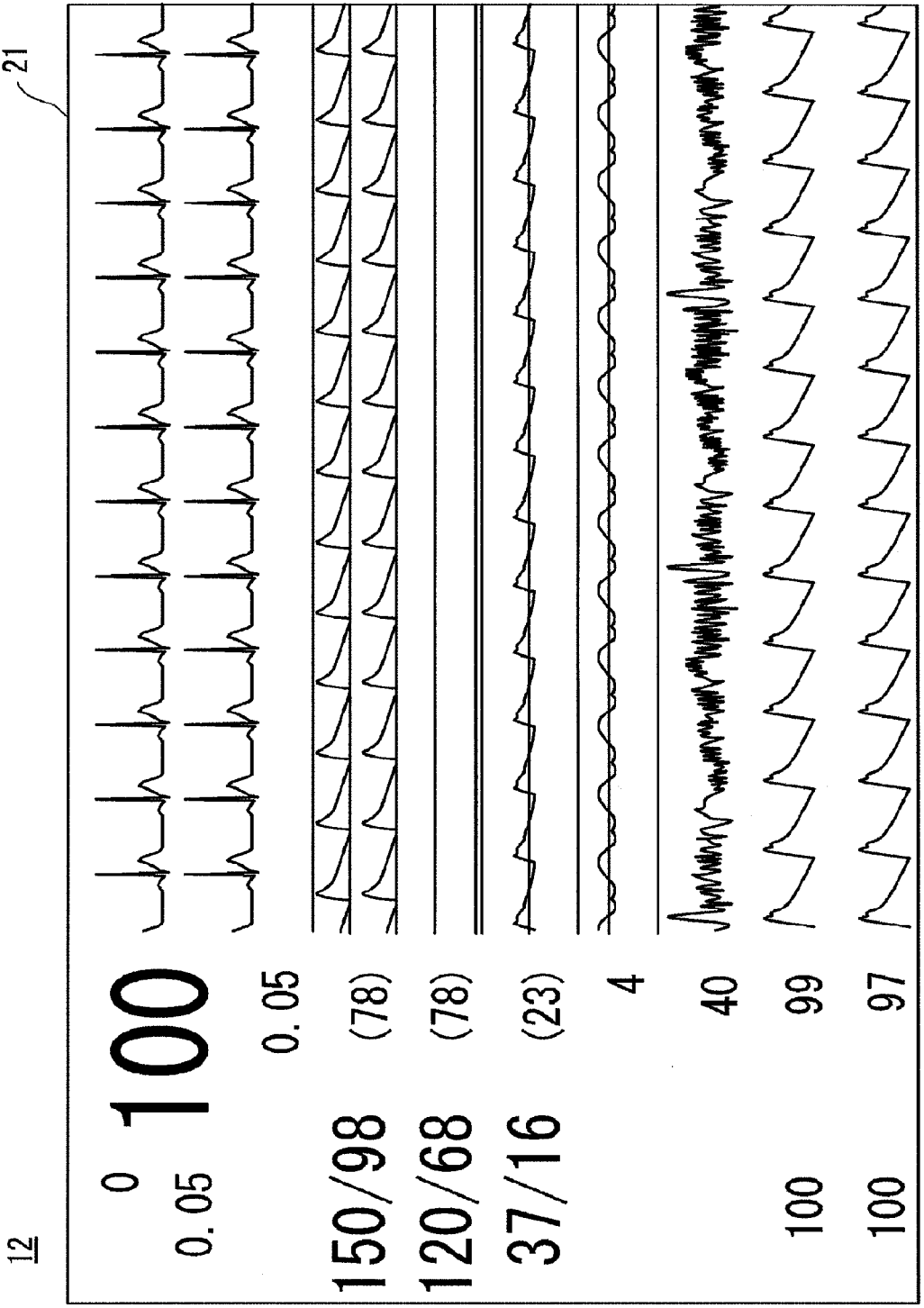
FIG. 2 is a view showing one example of a screen displayed on a displaying section in the monitoring apparatus of FIG. 1.

The displaying section 12 is disposed in a front face of the apparatus and serves as one example of a display. The display controlling section 13 is communicably connected to the signal receiving section 11 and the displaying section 12. As shown in FIG. 2, the display controlling section 13 causes the plural kinds of measurement signals which are received through the signal receiving section 11, to be displayed in real time on the displaying section 12.

The command receiving section 14 is communicably connected to the display controlling section 13. The command receiving section 14 is configured as a man-machine interface into which the operator inputs commands, and formed by buttons, switches, a mouse, a keyboard, and the like. At least a part of the displaying section 12 may be configured as a touch panel so as to serve as a part of the displaying section 12.

The operator can select at least one of the number and kinds of measurement signals which are to be displayed in real time on the displaying section 12, through the command receiving section 14. Namely, the display controlling section 13 serves as one example of a first display region former, and forms a first display region 21 in which at least one of the plural kinds of measurement signals is displayed in real time, on the displaying section 12.

The storage section 15 is communicably connected to the signal receiving section 11, and stores at least a part of the measurement signals which are sequentially received, as measurement data 31. The measurement data 31 is stored while being correlated with time information 32 that indicate the measurement time.

The monitoring apparatus 10 is configured to, in a case where, for example, a received measurement signal indicates an abnormal value, issue a visual and/or acoustic alarm. The storage section 15 is configured to store at least the measurement signal at the time when such an alarm is issued, as measurement data 31. Incidentally, the measurement data 31 is stored while being correlated with time information 32 indicating the time when the alarm is generated, and alarm information 33 indicating the kind of the abnormality.

Figure 3:
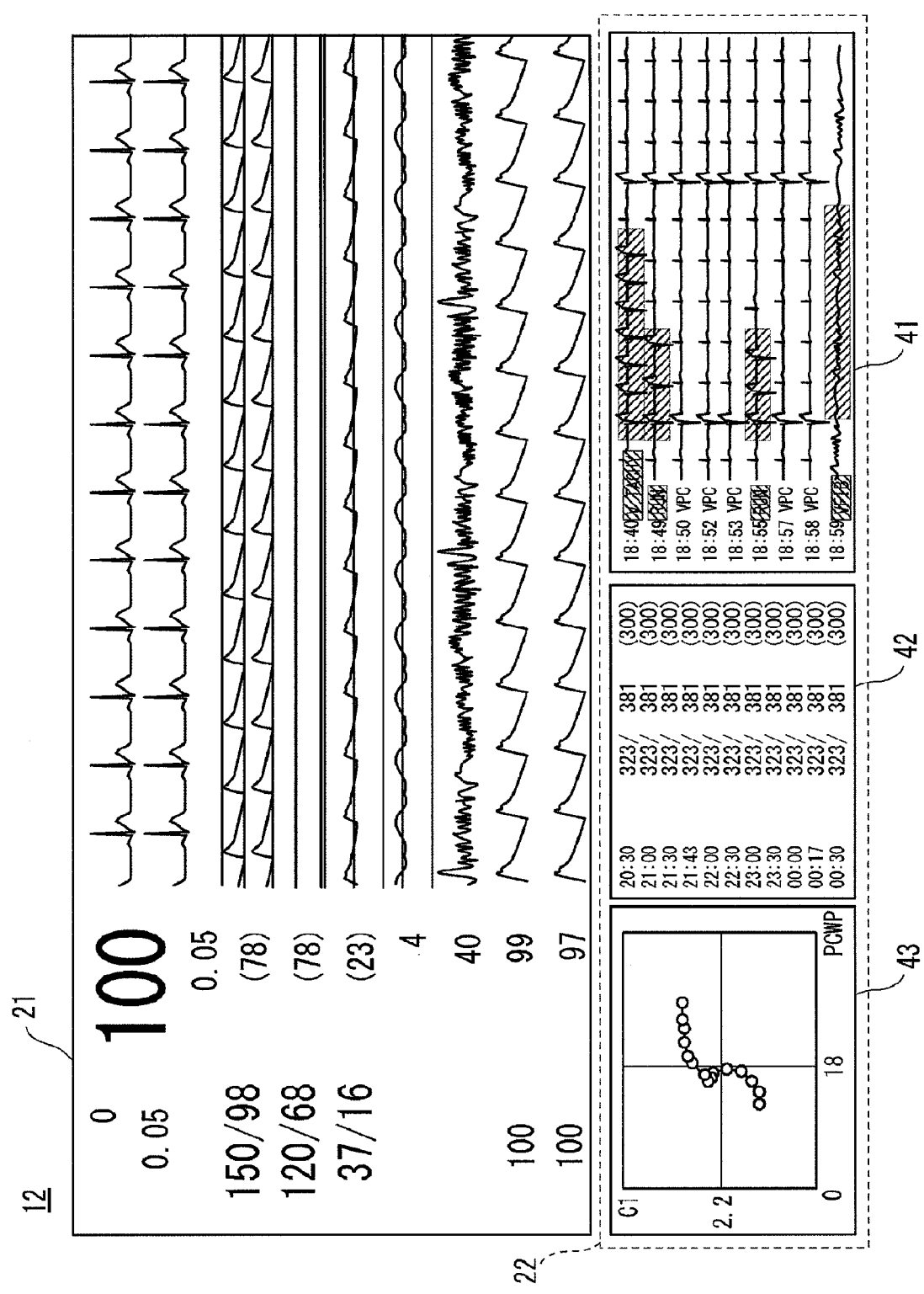
FIG. 3 is a view showing another example of a screen displayed on a displaying section in the monitoring apparatus of FIG. 1.

When a past measurement history of specific biological information of the subject is to be browsed, the operator performs a prescribed operation through the command receiving section 14, so that the display controlling section 13 causes a display region (second display region) 22 to appear on the displaying section 12 as shown in FIG. 3. The second display region 22 is used for the history browsing. Incidentally, the display controlling section 13 causes the first display region 21 to be displayed on the displaying section 12, while the area of the first display region 21 is reduced so as to avoid the second display region 22.

In the second display region 22, it is possible to display the history related at least arbitrary one of the plural kinds of measurement signals which are received by the signal receiving section 11. The kinds of the measurement signals are designated through the command receiving section 14.

The display controlling section 13 reads out the measurement data 31 stored in the storage section 15, for each designated measurement signal. In the second display region 22, a history display region for displaying a history is formed for each designated measurement signal, and the read out measurement data 31 is displayed in the history display region. As required, also time information 32 and alarm information 33 which are correlated with the measurement data 31 are read out to be displayed in the history display region.

In the example shown in FIG. 3, an arrhythmia history display region 41 for displaying a history of an arrhythmia alarm, an NIBP history display region 42 for displaying a measurement history of non-invasive blood pressure (NIBP), and a heart failure history display region 43 for displaying a history of Forrester classification are formed in the second display region 22.

In the arrhythmia history display region 41, an electrocardiogram waveform in which an arrhythmia is judged to occur is highlighted, and displayed in a list together with the measurement time of the electrocardiogram waveform and the kind of the alarm. In the NIBP history display region 42, the measurement value of the non-invasive blood pressure is displayed in a list together with the measurement time of the measurement value. The Forrester classification is a chart showing the severity of the heart failure of the subject based on the values of the pulmonary capillary wedge pressure (PCWP) which is obtained by a Swan-Ganz catheter, and the cardiac index (CI). In the heart failure history display region 43, the transition of the plotted position of the measurement value in the chart is shown.

As described above, the histories related to the measurement signals are displayed in any one of the forms of waveform, character, and graph. Alternatively, the histories may be displayed by chart such as workflow or illustration of the diagnostic method. A display mode in which two of these displays are adequately combined with each other may be employed.

Namely, the display controlling section 13 serves as one example of a second display region former, and forms the second display region 22 at a position where is not overlapping with the first display region 21 in the displaying section 12. The display controlling section 13 further serves as one example of a history presenter. The first and second history display regions which display respectively the histories related to the first and second measurement signals in the plural kinds of measurement signals are formed in the second display region 22. In the above-described example, for example, the NIBP history display region 42 corresponds to the first history display region, and one of the arrhythmia history display region 41 and the heart failure history display region 43 corresponds to the second history display region.

In this embodiment, in order to browse a past measurement history of specific biological information of the subject, the second display region 22 is formed at a position where is not overlapping with the first display region 21 where measurement signals are displayed in real time. Therefore, real-time viewing of measurement signals is not impeded even during a work of seeking or browsing a history. Moreover, since history displays respectively related to plural kinds of measurement signals can be displayed side by side in the second display region 22, the work of seeking or browsing a history can be efficiently performed while monitoring in real time the measurement signals.

In this embodiment, when it is not required to browse a history, the first display region 21 in which measurement signals are displayed in real time can be displayed on whole of the displaying section 12. Therefore, the real-time visibility of measurement signals is improved.

The display controlling section 13 is configured so that, when data which is in the history related to the first measurement signal, and which corresponds to a certain time are specified in the first history display region 21, those which are in the history related to the second measurement signal, and which corresponds to the time are displayed in the second history display region 22.

Figure 4:
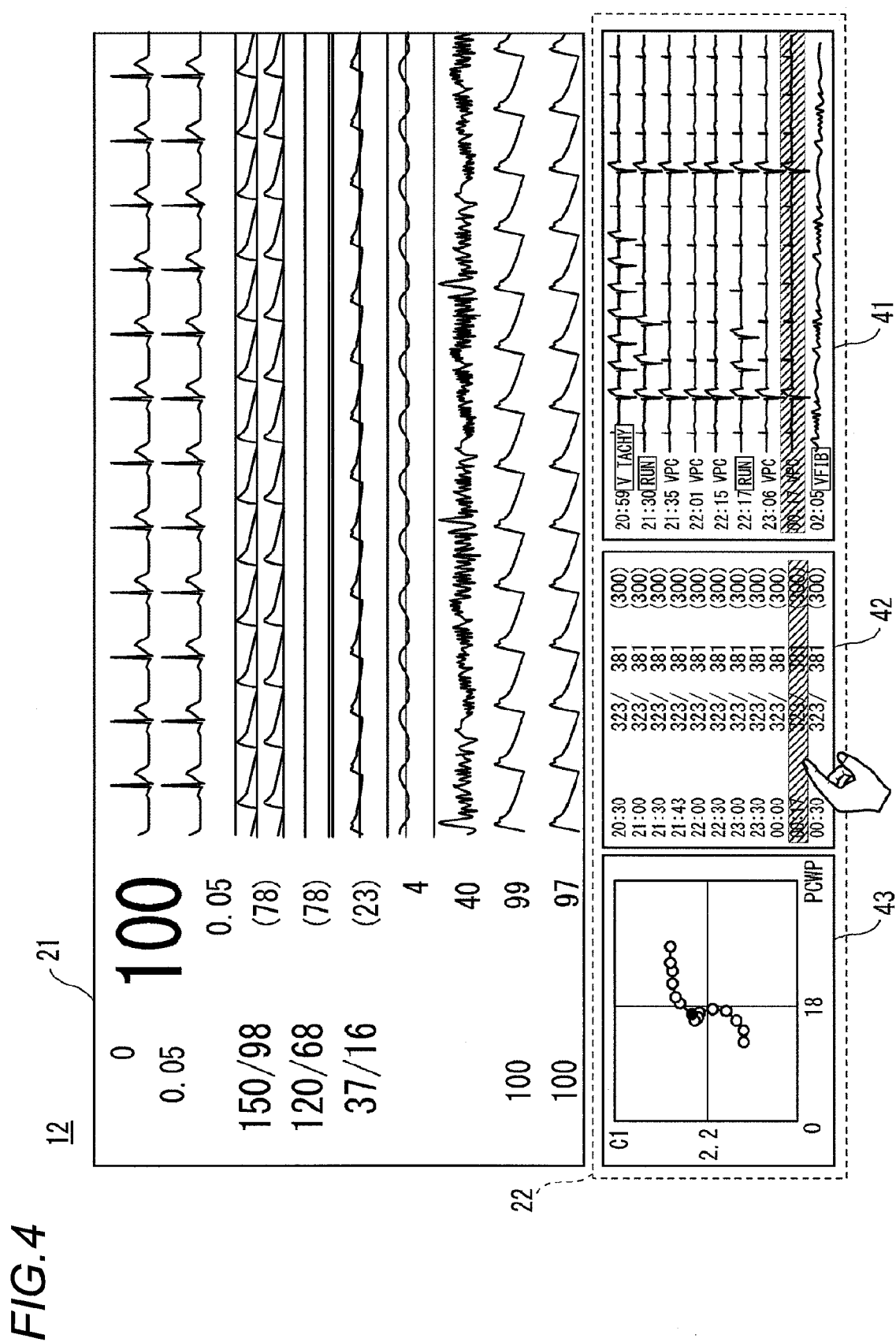
FIG. 4 is a view showing another example of a screen displayed on a displaying section in the monitoring apparatus of FIG. 1.

As shown in FIG. 4, for example, the operator specifies measurement data of the non-invasive blood pressure corresponding to the time "00:17" which is displayed in the NIBP history display region 42, through the command receiving section 14. The specifying of data is performed by, for example, a cursor or a tapping on a touch panel.

Based on the time indicated by the time information 32 correlated to the specified measurement data 31 of the non-invasive blood pressure, the display controlling section 13 reads out, from the storage section 15, the measurement data 31 which has the time information 32 corresponding to the time, and which is related to the arrhythmia alarm, and the measurement data 31 which is related to the Forrester classification. Here, "time information corresponding to" means the time information 32 indicating time which is identical with or close to the time indicated by the time information 32 correlated to the specified measurement data 31.

The display controlling section 13 causes the read out measurement data to be displayed in the history display regions. In the example shown in FIG. 4, when the measurement data of the time "00:17" displayed in the NIBP history display region 42 are specified, the display contents of the arrhythmia history display region 41 are changed, and the arrhythmia waveform at the time "00:17" is highlighted. In the heart failure history display region 43, the display color of the plot point corresponding to the time "00:17" is changed.

Generally, measurement data of biological information at a timing when an alarm is issued tend to exhibit a strong mutual correlation. According to the configuration of this embodiment, simply by specifying measurement data which is to be checked with respect to a certain measurement signal, measurement data of other measurement signals at a corresponding time are displayed in the history display regions. Therefore, it is possible to provide a display mode which is excellent in listing property, and in which a history can be efficiently sought or browsed.

The above-described effect is particularly remarkable in a case where, as in the example shown in FIG. 4, history display regions have different display modes. For example, a comparison between signal waveform-based measurement data and numeric-based measurement data tends to be more difficult than that between waveform-based measurement data, or that between numeric-based measurement data. According to the configuration of this embodiment, data related to different measurement signals are displayed side by side via time information, and therefore it is possible to support an efficient comparing work.

The display controlling section 13 is configured so that, during a period when measurement data is displayed by specifying the time as described above, updating of the history display in the history display regions is stopped.

In a case where, during a period when the list display is performed while specifying the time is executed as shown in FIG. 4, a new arrhythmia alarm occurs, for example, the display controlling section 13 does not perform a display operation to add a new alarm history to the arrhythmia history display region 41, but maintains the display state of FIG. 4. Therefore, the browsing work using the displayed list is not obstructed. The alarm information itself is displayed in the first display region 21, and therefore the operator can select one of interruption and continuation of the browsing work in accordance with the severity of the alarm.

The measurement data 31, time information 32, and alarm information 33 which are related to the new arrhythmia alarm are stored in the storage section 15. When the browsing state in which the time is designated through the command receiving section 14 is cancelled, the display controlling section 13 reads out the above-described information stored in the storage section 15, and updates the display to add the new alarm history into the arrhythmia history display region 41.

The monitoring apparatus 10 has an automatic operation mode in which, when the first measurement signal that is desired to be displayed is selected from the plural kinds of measurement signals, the second measurement signal that performs the history display in the second display region 22 is automatically selected, in addition to a manual operation mode in which, as described above, all measurement signals that cause respective measurement histories to be displayed in the second display region 22 are selected by the operator.

Relationship information 34 indicating the correlation between plural kinds of biological signals is stored in the storage section 15. The display controlling section 13 is configured so that, when the automatic operation mode is to be executed, a measurement signal having a strong relation with the biological information related to the selected first measurement signal is selected as the second measurement signal based on the relationship information 34 stored in the storage section 15, and the respective measurement histories are displayed in the second display region 22.

For example, the arrhythmia information displayed in the arrhythmia history display region 41 has a strong correlation with the measurement value of the non-invasive blood pressure which is displayed in the NIBP history display region 42. The correlation is stored as the relationship information 34 in the storage section 15. When the operator selects the measurement signal related to the arrhythmia information, as the object of history browsing (as the first measurement signal) through the command receiving section 14, the display controlling section 13 refers the relationship information 34, and selects the measurement signal related to the non-invasive blood pressure as the second measurement signal. As a result, as shown in FIG. 3, the arrhythmia history display region 41 and the NIBP history display region 42 are displayed in the second display region 22.

Insofar as displaceable in the second display region 22, two or more biological signals may be selected as signals having a strong relation. In this case, the display controlling section 13 refers the relationship information 34, and selects measurement signals related to biological information as those to be displayed in the sequence of strength of relation. In the case of the example shown in FIG. 3, a measurement signal related to the Forrester classification is selected subsequent to the measurement signal related to the non-invasive blood pressure, and the heart failure history display region 43 is displayed in the second display region 22.

According to the configuration, simply by selecting one measurement signal related to biological information, the operator can cause the history of a measurement signal related to biological information having a strong relation with the biological information, to be displayed in the second display region 22. With respect to sets of biological information having a strong correlation, there is a tendency that characteristic measurement data is simultaneously generated. Therefore, the efficiency of the work of reviewing a plurality of measurement data can be enhanced by specifying an occurring time of an alarm.

Figure 5:
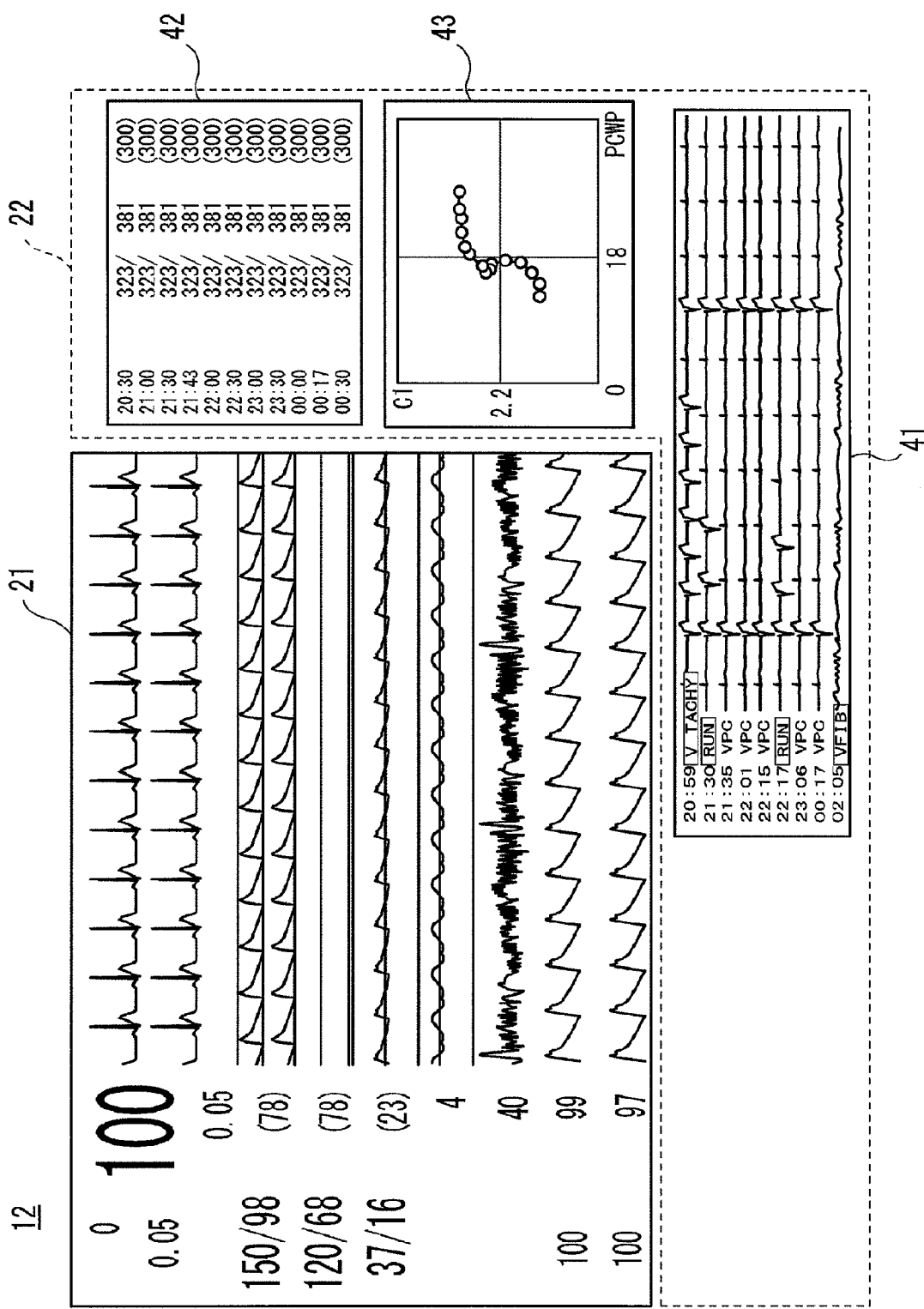
FIG. 5 is a view showing another example of a screen displayed on a displaying section in the monitoring apparatus of FIG. 1.

As shown in FIG. 5, the positions of the history display regions can be changed in the second display region 22. The shape of the second display region 22 can be changed in accordance with the arrangements of the history display regions. The first display region 21 is displayed in an adequately reduced size so as to avoid the second display region 22.

According to the configuration, the layout of the history display regions on the displaying section 12 can be changed as required. In the example shown in FIG. 5, the layout where the visibility of the arrhythmia waveform is enhanced is attained by laterally expanding the area of the arrhythmia history display region 41.

The display controlling section 13 is an arithmetic processing circuit which is configured by including an arithmetic device such as a CPU. The functions as the first display region former, the second display region former, and the history presenter can be realized by the operation of hardware such as circuit devices, that of software such as programs stored in the arithmetic device, or a combination of these operations.

The embodiment has been described in order to facilitate understanding of the invention, and is not intended to limit the invention. It is a matter of course that the invention may be changed or improved without departing the essence thereof, and includes equivalents thereof.

The second display region 22 may be always displayed on the displaying section 12 as far as it is formed at a position where is not overlapping with the first display region 21.

The disclosure of Japanese Patent Application No. 2012-037190 filed Feb. 23, 2012 including specification, drawings and claims is incorporated herein by reference in its entirety.

The invention claimed is:

1. A monitoring apparatus, comprising:
a display;
a receiver, configured to receive a plurality of kinds of measurement signals related to biological information of a subject;
a first display region former configured to form, on the display, a first display region in which at least one of the measurement signals is displayed in real time;
a second display region former configured to form, on the display, a second display region at a position that is not overlapping with the first display region; and
a history presenter configured to form, in the second display region, a first history display region displaying a history related to a first one of the measurement signals, and a second history display region displaying a history related to a second one of the measurement signals,
wherein when data corresponding to a certain time in the history related to the first one of the measurement signals is specified in the first history display region, the history presenter is configured to display, in the second history display region, data corresponding to the certain time in the history related to the second one of the measurement signals,
wherein the first history display region and the second history display region are concurrently displayed on the display having different display modes,
wherein the second display region former is configured to cause the second display region to appear on the display in accordance with a prescribed operation; and
wherein a displayed size of the first display region is reduced when the second display region appears so that the first display region and the second display region are not overlapped with each other on the display.

2. The monitoring apparatus as set forth in claim 1, wherein the history presenter is configured to stop updating the history displayed in the first history display region and the history displayed in the second history display region while the data corresponding to the certain time is displayed.

3. The monitoring apparatus as set forth in claim 1, wherein the history presenter is configured to cause a measurement signal related to biological information having a strong correlation with biological information related to the first one of the measurement signals, to be the second one of the measurement signals.

4. The monitoring apparatus as set forth in claim 1, wherein the history related to the first one of the measurement signals and the history related to the second one of the measurement signals are respectively displayed as a waveform, a character, a graph, or a chart.

5. The monitoring apparatus as set forth in claim 1, wherein a position of the first history display region and a position of the second history display region are respectively changeable within the second display region.

6. The monitoring apparatus as set forth in claim 1, wherein only the first display region is displayed on the display or both the first display region and the second display region are displayed on the display.

7. A monitoring apparatus, comprising:
- a display;
- a receiver, configured to receive a plurality of kinds of measurement signals related to biological information of a subject;
- a first display region former configured to form, on the display, a first display region in which at least one of the measurement signals is displayed in real time;
- a second display region former configured to form, on the display, a second display region at a position that is not overlapping with the first display region; and
- a history presenter configured to form, in the second display region, a first history display region displaying a history related to a first one of the measurement signals, and a second history display region displaying a history related to a second one of the measurement signals, wherein when data corresponding to a certain time in the history related to the first one of the measurement signals is specified in the first history display region, the history presenter is configured to display, in the second history display region, data corresponding to the certain time in the history related to the second one of the measurement signals, wherein the first history display region and the second history display region are concurrently displayed on the display having different display modes, wherein one of a state in which only the first display region is displayed on the display and a state in which both the first display region and the second display region are displayed on the display is selected, wherein the second display region former is configured to cause the second display region to appear on the display in accordance with a prescribed operation, and wherein a displayed size of the first display region is reduced so as to avoid the second display region appeared.

8. The monitoring apparatus as set forth in claim 7, wherein the history presenter is configured to stop updating of the history displayed in the first history display region and the history displayed in the second history display region while the data corresponding to the certain time is displayed.

9. The monitoring apparatus as set forth in claim 7, wherein the history presenter is configured to cause a measurement signal related to biological information having a strong correlation with biological information related to the first one of the measurement signals, to be the second one of the measurement signals.

10. The monitoring apparatus as set forth in claim 7, wherein the history related to the first one of the measurement signals and the history related to the second one of the measurement signals are respectively displayed as a waveform, a character, a graph or a chart.

11. The monitoring apparatus as set forth in claim 7, wherein a position of the first history display region and a position of the second history display region are respectively changeable within the second display region.

* * * * *